(12) United States Patent
Maier

(10) Patent No.: US 8,980,577 B2
(45) Date of Patent: Mar. 17, 2015

(54) MASS SPECTROMETRIC IDENTIFICATION OF HYPHAL FUNGI

(75) Inventor: Thomas Maier, Lilienthal (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 13/475,500

(22) Filed: May 18, 2012

(65) Prior Publication Data
US 2013/0309712 A1 Nov. 21, 2013

(51) Int. Cl.
G01N 27/62 (2006.01)

(52) U.S. Cl.
USPC .......................................................... 435/34

(58) Field of Classification Search
CPC ............... G01N 33/6848; G01N 33/56961; G01N 2333/37; C12Q 1/04
USPC .......................................................... 435/34
See application file for complete search history.

(56) References Cited

PUBLICATIONS

Pan et al., Identification of lethal Aspergillus at early growth stages based on matrix-assisted laser desorption/ionization time-of-flight mass spectrometry, Diagnostic Microbiology and Infectious Disease, 70: 344-354, published online May 4, 2011.*

Rueda et al., Changes in glycogen and trehalose content of Streptomyces brasiliensis hyphae during growth in liquid cultures under sporulating and non-sporulating conditions, FEMS Microbiology Letters, (2001) 194: 181-185.*

Alanio et al., Matrix-assisted laser desorption ionization time-of-flight mass spectrometry for fast and accurate identification of clinically relevant Aspergillus species, Clin. Microbiol. Infect., 17: 750-755, published online Jul. 29, 2010.*

Murray, Rapid Identification of Clinical Yeast Isolates by Mass Spectrometry, Curr. Fungal Infect. Rep., (2010) 4:145-150.*

Marklein et al., Matrix-Assisted Laser Desorption Ionization-Time of Flight Mass Spectrometry for Fast and Reliable Identification of Clinical Yeast Isolates, J. Clin. Microbiol., (2009) 47(9): 2912-2917.*

Elliot et al., (2012) Streptomycete Spores, In: eLS. John Wiley & Sons, Ltd: Chichester. DOI: 10.1002/9780470015902.a0000308.pub2.* van Baar, "Characterisation of Bacteria by Matrix-Assisted Laser Desorption/Ionisation and Electrospray Mass Spectrometry", FEMS Microbiology Reviews 24 (2000) 193-219.

* cited by examiner

Primary Examiner — Karen Cochrane Carlson
Assistant Examiner — Jennifer M. H. Tichy
(74) Attorney, Agent, or Firm — O'Shea Getz P.C

(57) ABSTRACT

A method is provided for identifying a hyphal fungus in a sample by similarity comparisons between a mass spectrum of the fungus and reference spectra. The method includes growing fresh hyphae without any adhering contact to surfaces as to form a mycelium with undifferentiated hyphae cells. A sample is prepared from the hyphae cells, and a mass spectrum is acquired of the hyphae cell sample. The mass spectrum is matched with at least one reference spectrum.

21 Claims, 2 Drawing Sheets

MASS SPECTROMETRIC IDENTIFICATION OF HYPHAL FUNGI

FIELD OF THE INVENTION

The invention relates to the field of determining a species of mycelium forming fungi ("hyphal fungi") by similarity comparison of a mass spectrum of their mycelium with reference mass spectra in spectrum libraries.

BACKGROUND OF THE INVENTION

Single cell microorganisms ("microbes") are routinely identified by mass spectrometric procedures in hundreds of microbiological labs all over the world, for instance for clinical diagnostics of infections, hygiene control in hospitals or bathing-establishments, or food analytics. Microbes may comprise bacteria, yeasts (single cell fungi), algae, or protozoa (e.g., plasmodia as pathogens of malaria). For all these microbes, identification procedures can be applied which utilize mass spectra of the essential cell components and compare those with reference spectra. In practice, this procedure is similar for all single cell species.

Hyphal fungi always form a mycelium. A mycelium is a mixture of fine threads, called "hyphae", forming chains of cells with one or more nuclei. The threads may form branches, and may be woven in a complex manner. Any growth takes place only at the tips of the hyphae, in contrast to the growth of algae threads which grow by cell division inside the threads. The terms "hyphal fungi" or "mycelium forming fungi" will here be used to separate these multi-cell fungi from single cell fungi like yeast.

Up to now, the mass spectrometric identification procedures fail to identify hyphal fungi, because the cells of the mycelium show fast differentiation, mainly concerning the metabolism which will be quickly adapted to environmental conditions. Cells differentiated in different ways show, after cell lysis, mass spectra which usually appear to be surprisingly different. Spores, fruit bodies, colonies in soil, or from surfaces of wood, cheese, bread or wall paper show mass spectra which, for the same fungus, are quite different. In most cases, they show relatively few outstanding mass signals. It has become known that relatively safe identifications may be achieved by limiting the analyses to spores only as a selected differentiation variety. It is, however, disadvantageous to have to wait during cultivation for the formation of spores which may last weeks or even many months. Besides, there are sometimes several forms of spores for the same fungus like asci spores, basidia spores, conidias, and others with different mass spectra in most cases.

Any identification is, in principle, the determination of the species and thus the positioning in the taxonomical hierarchy, reaching from the uppermost rank, the domain (archaea, bacteria, eukariota) down to order, family, genus, and species. Fungi form their own kingdom besides plants and animals. The result of any successful identification is the name of the species; this name offers access to all written information about this species.

Identification of hyphal fungi is essential in many areas: building trade, maintenance of woods or farm land, clinical diagnostics, food production, material storage, home hygiene and many others. The identification of fungi may become as essential as the identification of bacteria. Most interestingly, there are more than a hundred thousand known and described species of fungi, in contrast to only some ten thousand described species of bacteria.

In the last years, for microbes like bacteria, archaea, yeast, or single-cell algae, there have become known several biomolecular procedures of identification, like DNA or RNA sequencing or mass spectrometric measurement of cell ingredients. These procedures proved to be much faster and safer than classical identification procedures, with better rates for specificity (correct negative identification rate), sensitivity (correct positive identification rate) and other statistical error rates. It is highly desirable to develop similar procedures for fungi. Up to now, DNA sequencing has not really applicable because there are no unique sequence sections found for unique identifications, and often the polymerase chain reaction fails in the presence of fungus cell components; in contrast to the early international commitment to the 16S-sequences of ribosomal RNA (rRNA) for the unique identification of bacteria. Mass spectrometry is strongly affected by the strong and fast differentiation by adaption of the metabolism to environmental conditions.

The identification of bacteria by mass spectrometry is presented in some detail in the review article of van Baar (FEMS Microbiology Reviews, 24, 2000, 193-219: entitled "*Characterization of Bacteria by Matrix-assisted Laser Desorption/Ionization and Electrospray Mass Spectrometry*"). The identification is performed by similarity analyses between a spectrum of the bacterium to be identified with well-known reference spectra. For each similarity comparison with a reference spectrum, a similarity value is calculated. A bacterium may be regarded as identified if the similarity value for a distinct reference spectrum shows a clearly better similarity than the similarity values for all other reference spectra, and, in addition, a better value than a preselected similarity threshold.

The generation of mass spectra of microbes usually starts with the cultivation of clearly separated colonies (an "isolate") on a gelatinous culture medium in a Petri-dish. With a small swab, e.g., a wooden toothpick, a small amount of bacteria from the colony is spotted onto a mass spectrometric sample plate. The cells are lysed in a well-known way, a solution of matrix material is added and dried, and the sample plate is inserted into the ion source of a time-of-flight mass spectrometer (TOF) operated with ionization by matrix-assisted laser desorption (MALDI). Ions are generated by pulsed laser shots, and their flight time is measured. Usually hundreds of single spectra are added together to improve the signal-to noise ratio. The term "mass spectrum of a microbe" or in short "sample spectrum" always refers to this sum spectrum, added together from many single mass spectra.

As already mentioned, the identification is based on similarity analyses of sample spectra with reference spectra from a library. There are different kinds of similarity analysis procedures, dependent on the amount and quality of data stored in the reference spectra. A spectrum may include pairs of masses and intensities of ions only, or may contain additional information like widths and variations of widths of the mass signals, variations of the intensity values, percentage of appearance of a signal above detection limit, and so on. The literature shows a variety of different similarity calculation procedures, some aiming for fast calculations, others aiming for high identification quality. The assignee of the present invention, Bruker Daltronics, provides a fast and precise similarity analysis procedure (i.e., Bruker MALDI Biotyper™ identifier system) showing a high rate of success, as many independent studies were able to prove. This similarity procedure is essentially based on matching mass values, and less essentially on matching intensities.

The similarity values may be reduced, by a corresponding scale transformation, to easily recognizable numbers, for instance, to a maximum similarity (identity of spectra) with a similarity value of 3.00. The transformation may even be performed in such a way, that a similarity value of 2.00 is the minimum value for a safe identification of the species. It is our experience, that such a scale has a high psychological value for the acceptance of the procedure.

Hyphal fungi can be cultured on agar in Petri-dishes in the same way as bacteria, with special kinds of agar with some antibiotics to prevent simultaneous growth of bacteria. Usually a sample is swabbed onto the agar, sometimes resulting in a chaotic growth of isolates superimposing each other. Some tiny amounts of mycelium of these colonies may then be transferred to new agar plates. After a relatively short time, the growing colony already shows some differentiation of the mycelium: mycelium from the edges of the colony show mass spectra which are different from mycelium from the center. Thus the colonies on agar are not the best basis for mass spectrometric identification. In addition, picking pure mycelium for the acquisition of mass spectra sometimes is difficult; some agar picked with the mycelium may disturb sample preparation and spectrum acquisition.

There is a need for a bio-molecular, preferably a mass spectrometric procedure for the fast and safe identification of hyphal fungi, with an unequivocal determination of the species within one or two days.

SUMMARY OF THE INVENTION

An identification procedure is provided that is based on the selection of a unified differentiation stage of the mycelium cells for all the extraordinarily different hyphal fungi. The selection is, however, not directed towards a late development stage with completely differentiated cells, e.g., spores, but is based on a first development stage of the mycelium with as undifferentiated cells as possible. This calls for a cultivation which conserves the development stage of the freshly grown mycelium and prevents an early differentiation.

The cultivation proposed may be performed in a liquid cultivation medium, in such a way that the growing hyphae of the young mycelium cannot adhere at the walls of the container or at the surface of the liquid, because then a differentiation starts immediately. Small containers are used with a volume of about 10 milliliter, each filled to two thirds with a suitable cultivation broth. After inoculation with some mycelium grown on an agar in a Petri-dish, or with some hyphae harvested from mold, or with some cells of the fruit body of a mushroom, or with a few spores, young hyphae grow in all directions from the inoculated core, whereby the development stage of the hyphae is independent of the kind of original inoculation material. After inoculation, the container has to be continuously moved by headlong vertical rotation, e.g., in a slow rotator, to prevent adherence to walls or other surfaces. Deviations from the strict vertical alignment of the plane of rotation within about 45°, preferably about 30°, most preferred about 15°, may also be acceptable. Within about 20 to 24 hours, tiny filamentous flocks are grown, about a millimeter in diameter, with actinomorphic mycelium. Observed through a microscope, the flocks of different fungi have different appearance: mostly bright, sometimes dark, often fluffy, sometimes compact.

Within about ten minutes after cultivation, the flocks widely precipitate on the bottom of the container, if the container is standing upright. Using a pipette, the flocks can be sucked from the bottom together with about 1.5 milliliter of broth, and put into a centrifugation tube. They can be washed once or twice first with water, then with ethanol, and centrifuged accordingly. After removal of the last, ethanol, the pellet will be completely dried by evacuation in an exsiccator or a vacuum centrifuge. The dry but highly porous pellet will be soaked with about 20 to 50 microliter of formic acid (70 percent) that disrupts the cell walls almost immediately. Adding the same amount of acetonitrile and centrifuging forms a supernatant which can be used to prepare MALDI-samples on a mass spectrometric sample support. A favorable preparation method includes drying about one microliter of the supernatant, then adding another microliter of a solution of the matrix material. Drying again forms tiny crystals of the matrix material with embedded compounds, mostly proteins, out of the mycelium.

Mass spectra of these samples show more mass signals of about equal intensity as mass spectra of widely differentiated cells. They are also better reproducible and more characteristic. Presumably, the richness of mass signals results from the fact that no specialized metabolism was formed that strongly enriches a few cell components and thus suppresses many other mass signals. The mass spectra of the young mycelium are well suited for their identification by comparison with reference spectra obtained by the same cultivation and preparation method. The procedure can be used without any variation for very different kinds of fungi: mushrooms, molds, or pathogenic dermatophytes causing mycosis. The same mass spectrometers, and the same control and evaluation programs can be used as for the identification of bacteria, only a corresponding library of reference spectra has to be installed.

Reference spectra should be obtained without exception by the procedure using a continuously agitated liquid broth according to an aspect of the invention. For the identification of an unknown fungus, however, it is quite often possible and sufficient to harvest some fresh hyphae freely sprouting outwards from some elderly mycelium ("front mycelium"), in case such fresh mycelium is present. The front mycelium is fresh and undifferentiated, yielding mass spectra which are often practically identical with those obtained by the method of the invention, as many studies have shown. Only if this relatively simple and fast method does not succeed, a cultivation of some mycelium in liquid broth has to be applied. Front mycelium may be harvested from agars, but also from fungi growing wild.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
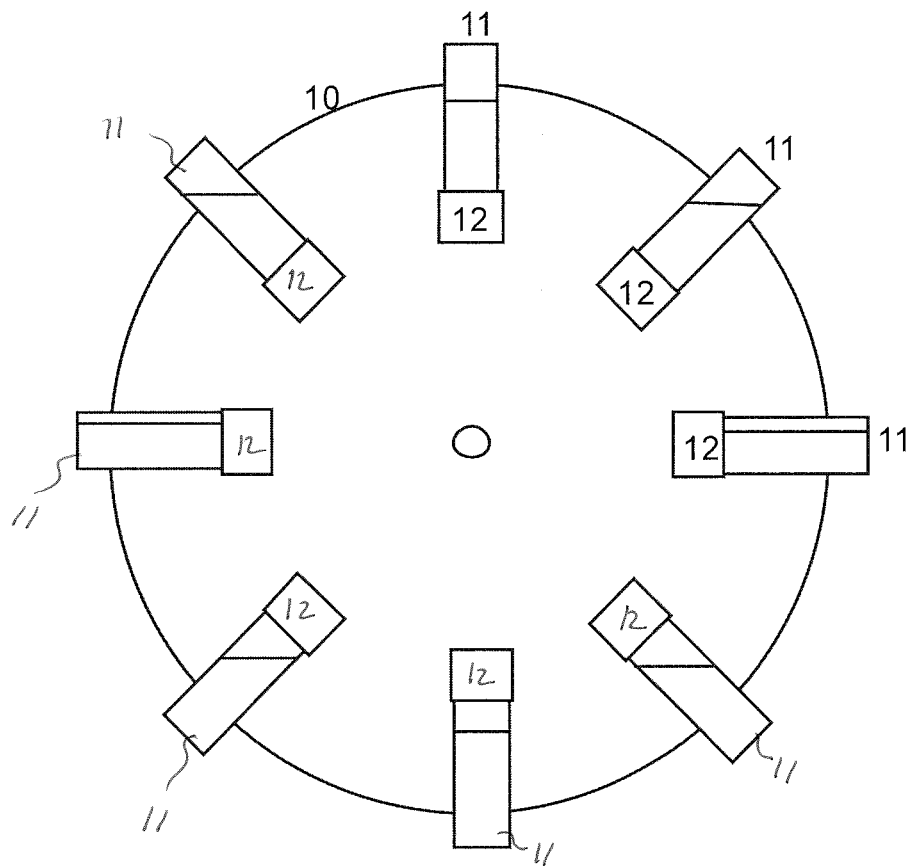
FIG. 1 schematically illustrates a rotator 10 with a plurality of cultivation tubes 11, closed by screw caps 12. The rotator keeps the tubes with the liquid broth in steady agitation by headlong vertical rotation. The rotator is operated with about 10 to 60 turns per minute, preferably with 20 to 30 rotations per minute.
Figure 2:
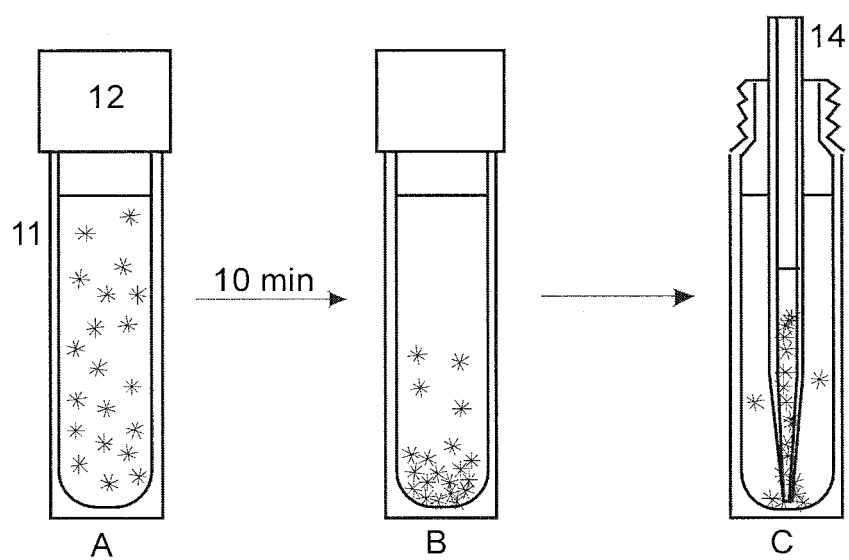
FIG. 2 illustrates how the flocks of young mycelium, being distributed evenly in the broth (A), precipitate in about 10 minutes (B), and can be removed by a pipette 14 from the bottom of the tube (C).
Figure 3:
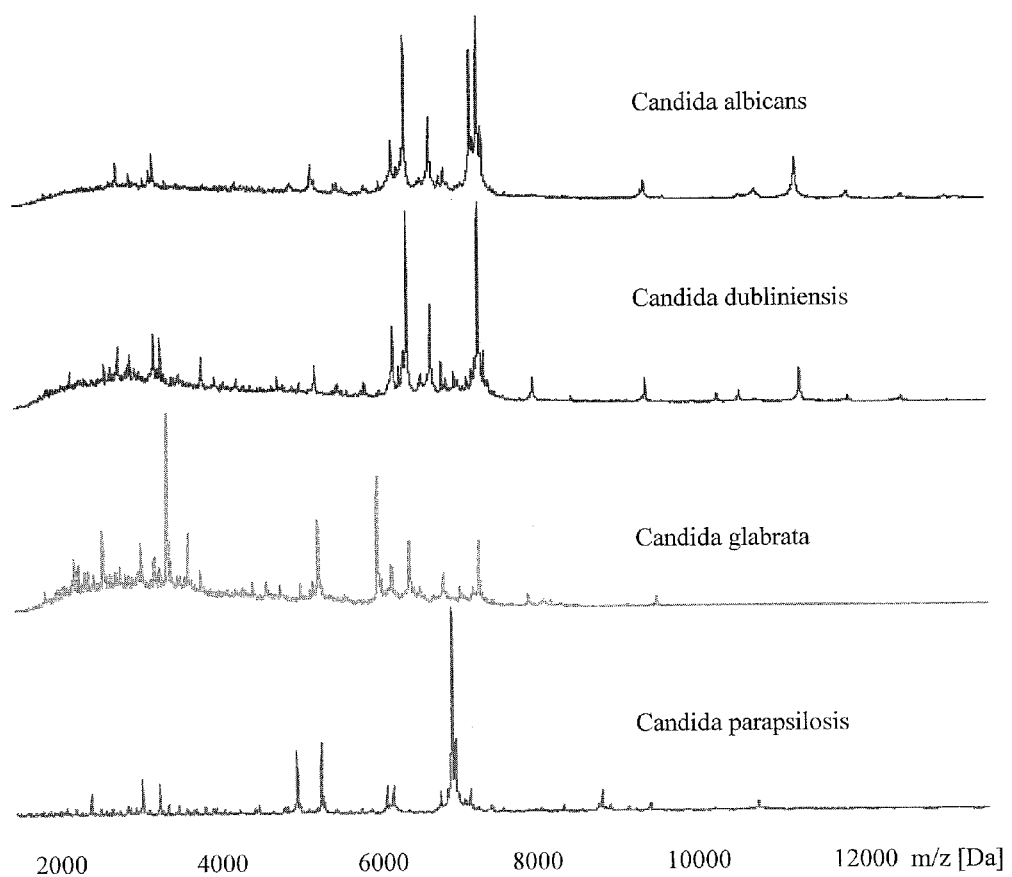
FIG. 3 shows, as examples for mass spectra of young mycelium, the mass spectra of different fungi of the genus *candida* (*candida albicans, candida dubliniensis, candida glabrata,* and *candida parapsylosis*).

The invention is based upon the selection of a unified stage of differentiation of the cells of the mycelium for the identification of the extraordinarily polymorphous hyphal fungi. Because differentiated fungal mycelium cells show widely different adaptions of their combustion to environmental conditions, young mycelium growing with undifferentiated hyphae are selected as this unified development stage. Standardizing on this first stadium of growth firstly offers much faster identification procedures than waiting for later differentiation stages, and secondly, it delivers mass spectra much more reliable for safe identification. The invention provides a technique to maintain young mycelium sufficiently long in this first stage of development. This needs a cultivation generating young mycelium and preventing any early differentiation.

Mycelium includes thin filaments with chains of cells, sometimes with single nuclei, sometimes with many nuclei. These filaments are called "hyphae". Growth takes place only at the tips of these hyphae, only exceptionally branching takes place from a point behind the tip. As soon as hyphae touch solid or liquid surfaces as, for instance, wood, paper, bread, but also glass, the hyphae adhere smoothly to these surfaces, and a chemical communication starts with the foreign surface. Thereby the metabolism will be changed; enzymes will be produced to digest material of the foreign surface, or toxins will be formed for defense against enemies. The formation of penicillin and other antibiotics against bacteria by fungi is well-known. The kind of adaption of the metabolism depends on the kind of foreign surface; the differentiated and surface-adapted cell is no longer suited for a mass spectrometric identification.

The term "differentiation of mycelium cells" only refers to the internal metamorphosis of the cell with respect to another metabolism, not to the kind of genetic differentiation of plant and animal tissue cells which is maintained during cell division. Differentiation of fungi cells is a more primitive procedure than those of higher organisms. Maintaining the differentiation stage during cell division cannot be expected for fungi, because growth takes place only at the tip of hyphae, foaming always fresh mycelium (the only exception is the formation of spores at the tip of hyphae). Any differentiation is a change of the metabolism of fungal cells; therefore, the cells of fresh mycelium may be correctly called "undifferentiated". Differentiated cell material, however, is strongly changed in its composition, changing correspondingly the mass spectra. For a communication with the environment, even the cell wall structure and composition will be changed.

Young, undifferentiated cells of the hyphae grow independently from the medium in which they grow. The hyphae do not take up any nourishment from the broth, they are fed by transport of the necessary components through the length of the hyphae from behind. This makes the fresh hyphae of front mycelium much alike, whether grown in liquids or in air. Mass spectra of hyphae growing in liquids or growing in air are quite often highly similar; even growth in different kinds of broth does only scarcely influence the mass spectra. The speed of growth of the hyphae may amount to one centimeter per day. In most cases, however, the speed is much slower.

The proposed cultivation of the inoculated cells in order to get undifferentiated mycelium will be performed in a liquid broth. The development stage of the inoculated cells does no longer play any role; within the broth always young, undifferentiated mycelium is produced. It must, however, be guaranteed that the mycelium produced cannot adhere to the wall of the container, or to the surface of the broth, because in these cases differentiation starts quickly. Preferably, containers are used with a volume of about 10 milliliters, commercially filled to about two thirds with a suitable broth, for instance "Sabouraud Liquid Broth". Inoculation may be performed with some mycelium grown as a colony in an agar-dish, but also with some cells from the fruit body of a mushroom, with some hyphae of mold, or with some spores. By this inoculation, immediately growth of young mycelium of an undifferentiated stage starts, no longer dependent on the differentiation of the material used as inoculation germ. The inoculation must be performed rather carefully in clean rooms because in environmental air there usually are between 500 spores (winter average) and 3000 spores (summer average) per cubic meter.

This young mycelium, undifferentiated in the sense described above, presents material with a unified development stage, outstandingly well suited for mass spectrometric identification. To avoid any differentiation caused by longer contact with surfaces, the small container must be continuously turned head-over-heels (somersault turns) by vertical rotation, preferably in a so-called rotator, as shown in FIG. 1. Certain deviations from a strictly vertical alignment of the plane of rotation may be acceptable. The agitation avoids any adherence to the walls of the container or the surface of the liquid. In this way, little flocks grow in the liquid broth, the size being in the range of one millimeter, ready to be harvested sometimes after 12 hours, in most cases after 20 to 24 hours. In rare cases, a cultivation of about 48 hours may be necessary.

Observed with a microscope, the spherical flocks of different fungi show quite different appearance: most often bright in color, only sometimes dark, mostly fluffy in its form, sometimes actinomorphic or even more compact. In most cases, they are specifically denser than the broth which shows a density of about 1.1 kilogram per liter. After stopping the movement and putting the container in upright position, they deposit at the bottom of the container after about 10 minutes. If the sinking speed of the flocks is too slow, some of the broth may be removed from the upper part of the container and replaced by pure water. Thereby the density of the broth is somewhat diminished, accelerating the deposition. If necessary, this procedure may be repeated until the flocks gather at the bottom.

The sediment of flocks can now be removed easily, together with about 1.5 milliliter of broth, by a pipette, and the young mycelium flocks can be transferred into a centrifugation tube, e.g., a 1.5 milliliter Eppendorf tube. They can be centrifuged to more sharply separate the flocks from the broth. If no clear pellet is produced, the stepwise replacement of the supernatant by water, as described above, may be applied. The pellet will be washed once or twice with water, then with ethanol, each time centrifuged for a short time of about a minute. The pellet will not be as hard as that obtained from bacteria, the pellet of fungi mycelium rather is somewhat fluffy. After complete removal of the last ethanol supernatant, the pellet will be completely dried by evacuation in an exsiccator or a vacuum centrifuge. Complete drying is essential for the fast destruction of the cell walls by the cell disruption process. The hard, but highly porous pellet is now soaked by formic acid (70 percent) or trifluoro-acetic acid. The amount of acid should be chosen such that the pellet is almost completely covered, for which usually about 10 to 50 microliter of acid is necessary. The acid penetrates into the porous pellet with access to all mycelium cells, opens the cell walls almost immediately, and transfers the soluble proteins and other soluble compounds into the liquid. After a short time of a few minutes, a same amount of an organic solvent like acetonitrile is added. Centrifuging precipitates the solid components, e.g., residues of the cell walls or even non-destroyed cells of old mycelium. The supernatant now can be used to prepare samples on a mass spectrometric sample support for ionization by MALDI. Most favorably, about one microliter of the supernatant is transferred to the sample support, dried, and covered by one microliter of a solution of matrix material. Suitable matrix materials like α-cyano-4-hydroxy-cinamonic acid (HCCA) or 2,5-Dihydroxybenzoic acid (DHB) and others are known to the specialist in the field. After drying again, tiny crystals of the matrix substance are produced, with evenly embedded mycelium compounds, well suited for ionization.

The samples on the sample support will be bombarded, in a time-of-flight mass spectrometer, with focused UV laser pulses, whereby ions are generated from the most highly concentrated mycelium compounds. This procedure is well-known by the acronym "MALDI", "ionization by matrix-supported laser desorption". Most of the ions are generated from protein and peptide molecules, with masses characteristic for the species of the fungus.

The mass spectra of the samples prepared by this procedure are richer in mass signals above background, better reproducible and more characteristic as mass spectra from differentiated material. Presumably, the richness in mass signals shows that no change of the metabolism has been occurred, because a change in the metabolism usually favors the generation of high concentrations of only a few compounds, suppressing others. The mass spectra of young mycelium are well suited for the identification of the hyphal fungi by similarity comparisons of their mass spectra with reference spectra from a library. This procedure is applicable, without any changes, to pathogenic filamentous fungi (e.g. athlete's foot or nail infections), fungi from infections of human or animal tissue (mycosis), molds, wood fungus, or mushrooms. The same mass spectrometer, and the same control and evaluation software may be used as for the identification of bacteria or other single-cell organisms; a corresponding library of reference spectra is needed. The reference spectra should be generated by the procedure with cultivation in continuously moved liquid broth, as described above.

Some samples of mycelium of unknown fungi show hyphae freely sprouting outwards into the air like hair (front mycelium), sometimes a few millimeters long, sometimes shorter. These hyphae likewise form young, in most cases undifferentiated mycelium. Quite often, it is just sufficient to harvest some of this front mycelium (if it is possible to harvest such front mycelium which is not always easy), and to wash and prepare this front mycelium as described above for the flocks grown in broth. In many cases this front mycelium delivers mass spectra directly usable for identification, as many studies have shown. The front mycelium may be harvested from agar plates, but sometimes also from fungi growing wild. This procedure is much faster and simpler than any cultivation in broth and results in a very early identification. But this procedure is not always successful, sometimes the mass spectra are different from those of this fungus species in the reference library. When this procedure does not show any success of identification by sufficiently high similarity values, the cultivation in continuously moved broth has to be applied. Up to now, this fast procedure of harvesting hyphae has not shown any misidentification.

Mass spectra of different species of hyphal fungi may even be used to determine the degree of relationship between different species. Similarity values between mass spectra of different species may be transformed directly into relationship distances, and can be used to construct a "dendrogram" describing the phylogenetic relationship. In this way, the taxonomic relations determined hitherto by microbiologists may be corrected by mass spectrometric means. Mass spectrometry may have the chance to become a kind of "gold standard" for taxonomical classifications.

The procedures described here may be modified, in knowledge of this invention, by specialists in the field in many ways. Only a few of these variations are pointed to above. There are more procedures based upon the selection of undifferentiated mycelium according to this invention.

Although the present invention has been illustrated and described with respect to several preferred embodiments thereof, various changes, omissions and additions to the form and detail thereof, may be made therein, without departing from the spirit and scope of the invention.

What is claimed is:

1. A method for the identification of a hyphal fungus in a sample by similarity comparisons between a mass spectrum of the fungus and reference spectra, comprising:
   growing fresh hyphae in liquid broth in a container without any adhering contact to surfaces as to form a mycelium with undifferentiated hyphae cells wherein the container is continuously rotated in a plane not coinciding with a horizontal plane;
   preparing a sample from the hyphae cells;
   acquiring a mass spectrum of the hyphae cell sample; and
   matching the mass spectrum with at least one reference spectrum.

2. The method according to claim 1, wherein the plane of rotation is aligned vertically.

3. The method according to claim 1, wherein the cultivation is performed for a time between 12 and 48 hours.

4. The method according to claim 3, wherein the cultivation takes between 20 and 24 hours.

5. The method according to claim 1, wherein the liquid broth is inoculated with cells from fruit body of a mushroom, with hyphase of mold, or with spores.

6. The method according to claim 1, wherein the liquid broth is inoculated with fungus mycelium from a colony cultivated on agar.

7. The method according to claim 1, wherein, after cultivation, mycelium flocks grown in the liquid broth are precipitated by one of centrifugation and gravity, and taken out with a pipette.

8. The method according to claim 7, wherein the mycelium flocks are transferred into a centrifugation tube, washed, and subjected to cell disruption.

9. The method according to claim 8, wherein the mycelium flocks in the centrifugation tube are washed first with water, then washed with ethanol, and finally completely dried by evacuation before being subjected to cell disruption.

10. The method according to claim 9, wherein cell disruption is performed by the addition of acid.

11. The method according to claim 10, wherein formic acid or trifluoro-acetic acid is used for cell disruption.

12. The method according to claim 10, wherein additionally an organic solvent is added and the disrupted cells are centrifuged.

13. The method according to claim 12, wherein the organic solvent is acetonitrile.

14. The method according to claim 13, wherein, after centrifuging the disrupted cells, a small quantity of the supernatant is transferred to a mass spectrometric sample support and a mass spectrometric sample for ionization by matrix-assisted laser desorption is prepared with a small amount of a matrix material solution.

15. The method according to claim 14, wherein the quantity of supernatant on the sample support plate first is dried, then covered with the matrix solution and dried again.

16. The method according to claim 14, wherein a mass spectrum is acquired from the mass spectrometric sample on the sample support, and the fungus is identified by similarity comparisons of the sample spectrum with reference spectra.

17. The method according to claim 1, wherein the container is continuously moved by headlong vertical rotation.

18. The method according to claim 17, wherein the plane of rotation deviates from the vertical alignment within about 45°.

19. The method according to claim 1, wherein the rotational axis is outside the container.

20. The method according to claim 1, wherein the surface is one of the walls of the container or the surface of the liquid broth.

21. A method of the identification of a hyphal fungus in a sample by similarity comparisons between a mass spectrum of the sample and reference spectra wherein
   the cells of the hyphal fungus are harvested from front mycelium growing on the fungus samples, subjected without further cultivating to cell disruption, and used for identification by similarity comparisons; and
   the reference spectra are obtained after cultivation of hyphal fungi in a liquid broth which is continuously rotated in a plane not coinciding with a horizontal plane.

* * * * *

UNITED STATES PATENT AND TRADEMARK OFFICE
CERTIFICATE OF CORRECTION

PATENT NO. : 8,980,577 B2  
APPLICATION NO. : 13/475500  
DATED : March 17, 2015  
INVENTOR(S) : Maier Page 1 of 1

It is certified that error appears in the above-identified patent and that said Letters Patent is hereby corrected as shown below:

In the Specification

Column 5
Line 38, please delete "foaming" and insert --forming--

Signed and Sealed this
Twenty-third Day of June, 2015

Michelle K. Lee
*Director of the United States Patent and Trademark Office*